United States Patent [19]

Orlowski et al.

[11] Patent Number: 5,141,436
[45] Date of Patent: Aug. 25, 1992

[54] METHOD OF BONDING ARTICLE TO TEETH EMPLOYING A LIGHT CURABLE PRIMER

[75] Inventors: Jan A. Orlowski, Altadena; David V. Butler, West Covina, both of Calif.

[73] Assignee: Scientific Pharmaceuticals, Inc., Duarte, Calif.

[21] Appl. No.: 434,180

[22] Filed: Nov. 13, 1989

[51] Int. Cl.⁵ .............................................. A61C 5/04
[52] U.S. Cl. ................... 433/226; 433/228.1; 433/9
[58] Field of Search ................... 433/228.1, 226, 9

[56] References Cited

U.S. PATENT DOCUMENTS 4,952,142  8/1990  Nicholson .............................. 433/9

*Primary Examiner*—V. Millin
*Attorney, Agent, or Firm*—Cushman, Darby & Cushman

[57] ABSTRACT

A method of bonding polymeric articles to tooth structures employing a light curable primer, including etching the surface of said tooth, applying a primer to the polymeric article the primer including light curable acrylate or methacrylate monomers and a volatile solvent which softens or partially dissolves the polymeric material of the article, applying light curable adhesive to the article or tooth, and applying the article to the tooth and curing the primer and the adhesive by applying light.

6 Claims, No Drawings

METHOD OF BONDING ARTICLE TO TEETH EMPLOYING A LIGHT CURABLE PRIMER

BACKGROUND OF THE INVENTION

The present invention relates to methods of light induced dental bonding, primer compositions and bonding procedures and in particular to primers for bonding dental appliances to teeth.

Photopolymerization techniques provide significant advantages when used to bond articles to tooth structures. The light curable materials typically employed in photopolymerization techniques have excellent shelf life, simplicity of their handling, convenience of long working time, economy of material use and reproducibility of results with respect to bonding strength. These are the main advantages of this technique, over prior techniques, which used chemically cured adhesives. Although ultra violet (UV) and visible light cured adhesives/cements for bonding metal or ceramic orthodontic brackets and other dental appliances are well known and described in the patent, scientific and commercial literature (see, for example, Jan A. Orlowski, David C. Walters U.K. patent application 2,006,792 and Richard J. Bennett U.S. Pat. No. 4,801,528), the attempts to use such materials to bond plastic appliances to teeth, and especially to bond orthodontic brackets commonly made of polycarbonate material, were unsuccessful.

Certain self cured formulations have proven successful for bonding articles made of polycarbonates. These contain lower molecular weight monomethacrylate resins, or utilize such resins as primers, to condition bracket surfaces. Lower molecular weight monomethacrylates have the ability to soften polycarbonate material and enhance adhesion. They can also be cured at low temperatures using proven peroxide/amine free radical generating systems.

These monomers are, however, difficult to cure, under acceptable clinical conditions, when using UV or visible light to induce polymerization. Therefore, the lower molecular weight monomethacrylates are not considered suitable for use as major components of light cured adhesives designed for plastic, and more specifically polycarbonate brackets, or for use as components of the primer for such brackets which is applied beneath light cured adhesives/cements.

A great problem exists of finding light curable adhesives for bonding plastic brackets to teeth. This problem is gaining in importance for the following reasons:

1. Current trends show great demand for developing aesthetically superior translucent, clear or tooth colored brackets;
2. Light curing materials are especially suitable for use with such brackets because the adhesive may be quickly, and easily cured by direct irradiation through the brackets;
3. A light curing technique allows the clinician to work without time pressure, as he is in full control of the curing process. The handling of the adhesive and removal of the excess are considerably easier than that for chemically cured materials;
4. Light cured materials are more thermally stable (they do not require refrigeration), color stable, and more economical in use than chemically cured counterparts;
5. Reproducibility of bonding strength with light cured materials is better than with chemically cured materials; and
6. Substantial progress has been made lately in developing reinforced plastic (such as polycarbonate) brackets by inserting metal arch wire slots and/or incorporating inorganic fillers or fibers into the polymer.

Unfortunately, known compositions and procedures do not provide an acceptable solution for intra-oral bonding of plastic brackets, using light (i.e. near ultraviolet or visible) curable adhesives.

The present invention has solved this problem by providing excellent photopolymerizable resin primer compositions and bonding procedures for bonding plastic dental appliances to teeth.

SUMMARY OF THE INVENTION

The present invention provides workable simple and dependable primer compositions, methods of employing same and techniques for bonding plastic dental appliances to teeth using light curable adhesives. The bonding procedure according to this invention includes applying in a first step, an etching agent such as phosphoric acid or citric acid to the tooth enamel. After sufficient etching, the etching agent is rinsed off with water and dried. A clean, dry field is maintained. The primer of the present invention is applied to the orthodontic article which will be bonded to the tooth. An adhesive is applied to the tooth and/or the article. The adhesive may be a wide variety of ethylenically unsaturated polymerizable compositions preferably, acrylic esters, acrylated polyesters or acrylated polyurethanes. The article is applied to the tooth and the primer and adhesive are cured using a light (visible or near ultra violet) induced polymerization technique.

The primer consists of a light curable resin including acrylate and/or methacrylate monomers e.g. di-, tri- or polymethacrylate monomers and, optionally, polymerization initiators and/or activators and a volatile solvent capable of softening, or partially dissolving, the plastic material of which the article to be bonded is made. Such compositions may also include thickening agents, fillers, coloring agents, antioxidants, stabilizers and other additives commonly used for improving or altering the characteristics of the light curable materials.

According to a preferred embodiment of this invention, an orthodontic appliance, such as an orthodontic bracket, is first primed with a composition comprising a solvent, or mixture of solvents, able to affect the polymeric material by partially dissolving and/or softening it, and light curable esters of acrylic or methacrylic acids. Preferably, but not necessarily, such blend should also contain light inducible polymerization initiators/activators, stabilizers, antioxidants, and selective light wavelength absorbers.

Because the majority of bonded plastic appliances in dentistry are made totally, or in part, of a polycarbonate-type material, the solvents used in preferred embodiments of this invention are halogenated derivatives of methane and ethane, and more preferably: chloroform; 1,2-dichloroethylene; 1,1,2,2-tetrachloroethane; and methylene chloride. Less preferred solvents to dissolve or soften the polycarbonate resin are pyridine, p-dioxane and cresylic acid. These are less desirable because of their lower volatility and/or toxicity.

The primer composition contains 20-99% but preferably 20-96% of the volatile solvent. The solvent, preferably, has a boiling point of 35°-120° C. at atmospheric pressure.

In one embodiment of the present invention, a substantial part of the solvent is allowed to evaporate prior to bonding.

The polymerizable resin component may consist of one, or a blend, of acrylate or methacrylate esters, at least one of them containing two or more ethylenically unsaturated groups per molecule. Preferably, at least 50% of the light curable acrylate or methacrylate monomers contain two or more ethylenically unsaturated groups per molecule. Methacrylate esters are preferred over the acrylates because they are less toxic. Examples of such esters are; Bisphenol A diglycidyl ether dimethacrylate (known as Bis-GMA) and its derivatives; Bisphenol A di(methacroylethyl) ether (known as EBA); 7,7,9-trimethyl - 4,13-dioxo - 3,4-dioxa - 5, 12-diazahexadecane 1,16-diol - dimethacrylate (known as diurethane dimethacrylate), ethylene - , diethylene - , triethylene - , tetraethylene - and corresponding propylene - glycol dimethacrylates, 1,6-hexamethyleneglycoldimethacrylate, trimethylolpropane-trimethacrylate, and neopenlylglycoldimethacrylate.

After application of the primer to the orthodontic article and subsequent partial, or total evaporation of the solvent, in one embodiment of the present invention, photoinitiation of the resin can be best accomplished using carbonyl - group containing initiators. The choice of an initiator and its concentration depends on the intensity and wavelength characteristic of the light source, as well as on reactivity of the monomers used in the formulation. Examples of photoinitiators used are: benzoin, benzoin ethers, alpha-substituted benzoins, antraquinones, substituted antraquinones, benzil, as well as alpha, beta diketones, such as camphoroquinone and naphthoquinone. Certain reducing agents, are desirable as polymerization activators, especially those of tertiary amine - type. The reducing agent preferably consists of tertiary amines containing N-substituted aliphatic groups. Examples of such reducing agents are: tributyl-amine, tripropylamine, alkyl-, dihydroxyalkyl-amines, methacroyl- (or acroyl-) alkyl-, dialkylamines, for example, methacroyl-C(2-5) alkyl-di-C(1-5) alkylamine. Methacroyl-alkylamines are preferred because of their ability to co-polymerize with other methacrylate resins, when the material is being cured.

Further examples of polymerization activators are diethyloaminoethyl methacrylate and methyl-bis-(2-hydroxyethyl-)amine.

The cure is accomplished by visible light having wavelengths of about 410-770 nanometers or by near ultraviolet light having wavelengths of about 300-410 nanometers.

An example of an ultraviolet absorber is 2-hydroxy-4-methoxy benzophenone.

An example of a filler is silicone dioxide.

Examples of stabilizers that may be used to extend the shelf life of the formulations of this invention and increase their resistance to elevated temperatures are:

2,6 - di- tert- butyl phenol;
2,2',4,4' - tertrahydroxybenzophonone;
2 - hydroxy - 4 - methoxy - benzophenone - 5 - sulfonic acid;
2,6 - di- tert- butyl- alpha- di-methylamino - p - cresol;
2,6 - di- tert- butyl cresol; and
tert- butyl- hydroxytoluene (BHT).

DETAILED DESCRIPTION OF THE INVENTION

The following examples will provide a better understanding of the invention. They are presented, however, only for the purpose of illustration, without limiting the scope of this invention.

EXAMPLE 1

The labial surfaces of maxillary cuspid, extracted human teeth, were etched for 30 seconds with 30% solution of a phosphoric acid, followed by rinsing with water and drying with a 40° C. air stream. Concurrently, the bases of the plastic orthodontic brackets, maxillary cuspid-type, manufactured from polycarbonate material by Tella-Tech Inc., 12860 Biscayne Blvd., North Miami, Fla. 33161, were treated for 2 minutes with a formulation consisting of:

| Ingredient | Weight % |
|---|---|
| methylene chloride | 80.0 |
| Bis-GMA | 12.0 |
| 1,6-hexamethyleneglycol dimethacrylate | 7.8 |
| camphoroquinone | 0.05 |
| diethyloaminoethyl methacrylate | 0.14 |
| tert- butyl-hydroxytoluene (BHT) | 0.01 |

The brackets were thereafter bonded to the teeth using "Eclipse" brand, visible light cured orthodontic adhesive, manufactured by Scientific Pharmaceuticals, Inc., 1828 Evergreen Street, Duarte, Calif. 91010, and "Optilux" brand curing instrument by Demetron Research Corporation, 5 Ye Olde Road, Danbury, Conn. 06810. The curing technique used was basically the same as recommended by the manufacturer of the adhesive, with the light being directed through the bracket. Such an approach is preferred, although not exclusive, for plastic brackets, because of their permeability by light. The curing time was 40 seconds per bracket.

The strength necessary to separate the brackets from teeth was determined under tensile forces. Control tests involved brackets bonded in an identical way but without the use of a bracket primer as described above. The result of the tests are given in the table below:

| | Bonding Strength (lbs) | |
|---|---|---|
| | With Primer | Without Primer |
| Average of six brackets | 23.6 | 2.6 |
| Range | 21-29 | unmeasurable-5 |

EXAMPLE 2

Tooth surfaces were prepared as described in Example 1. The following formulation was applied on the polycarbonate orthodontic bracket base.

| Ingredient | Weight % |
|---|---|
| diurethane dimethacrylate | 3.0 |
| Bis-GMA | 5.0 |
| triethyleneglycol dimethacrylate | 2.0 |
| silicone dioxide | 3.0 |
| BHT | 0.006 |
| 2-hydroxy-4-methoxy benzophenone | 0.04 |
| camphoroquinone | 0.044 |

-continued

| Ingredient | Weight % |
| --- | --- |
| methyl-bis-(2-hydroxyethyl-)amine | 0.05 |
| chloroform | 76.81 |

After 3 minutes warm air of approx. 45° C. was blown on the bracket base in order to accelerate the evaporation of the solvent, followed by bonding of the brackets to the etched area of the teeth as described in Example 1.

The results of bonding strength tests were comparable with those described in Example 1.

EXAMPLE 3

The procedure of bonding and the adhesive system were the same as described in Example 1, but the brackets used were made of polycarbonate material 25% filled with silica. The measured bonding strength on 10 specimens was in the range of 22–31 lbs. with an average of 24.2 lbs.

EXAMPLES 4A AND 4B

Further exemplary compositions of the present invention are the following:

| Example 4A | |
| --- | --- |
| Ingredient | Weight % |
| methylene chloride | 80 |
| Bis-GMA | 12 |
| 1.6-hexamethyleneglycol dimethacrylate | 8 |

| Example 4B | |
| --- | --- |
| Ingredient | Weight % |
| methylene chloride | 80 |
| diurethane dimethacrylate | 20 |

Both of the above compositions in Examples 4A and 4B would provide adequate bonding strength when employed in a bonding procedure such as described in Example 1.

While only a few exemplary embodiments of this invention have been described in detail, those skilled in the art will recognize that there are many possible variations and modifications which may be made in the exemplary embodiments while yet retaining many of the novel and advantageous features of this invention. Accordingly, it is intended that the following claims cover all such modifications and variations.

What is claimed is:

1. A method of bonding polymeric articles to tooth structures, comprising the following steps:
   etching the surface of said tooth;
   applying a primer to said polymeric article said primer including light curable acrylate or methacrylate monomers and a volatile solvent which softens or partially dissolves the polymeric material of said article;
   applying light curable adhesive to said article or tooth; and
   applying said article to said tooth and curing said primer and said adhesive by applying light.

2. The method of claim 1 wherein said bonded article is an orthodontic appliance.

3. The method of claim 1 wherein said bonded article is an orthodontic bracket.

4. The method of claim 1 further including the step of evaporating a substantial part of said solvent prior to curing.

5. The method of claim 1 wherein said light for curing is visible light having wavelengths of about 410–770 nanometers.

6. The method of claim 1 wherein said curing light is near ultraviolet light having wavelengths of about 300–410 nanometers.

* * * * *